United States Patent [19]

Schlegel

[11] Patent Number: 4,706,669
[45] Date of Patent: Nov. 17, 1987

[54] DEVICE FOR PERFORATING THE LENS CAPSULE FRONT WALL IN THE EYE OF LIVING BEINGS

[76] Inventor: Hans-Joachim Schlegel, Max-Planck-Street 5, Bad Homburg, Fed. Rep. of Germany

[21] Appl. No.: 783,934
[22] PCT Filed: Jan. 30, 1984
[86] PCT No.: PCT/DE84/00024
§ 371 Date: Sep. 26, 1985
§ 102(e) Date: Sep. 26, 1985
[87] PCT Pub. No.: WO85/03217
PCT Pub. Date: Aug. 1, 1985
[51] Int. Cl.[4] .......................... A61F 9/00; A61B 17/32
[52] U.S. Cl. .................................. 128/329 R; 128/305
[58] Field of Search .............. 128/305, 329 R; 604/22

[56] References Cited

U.S. PATENT DOCUMENTS

| 4,210,146 | 7/1980 | Banko | 128/305 |
| 4,246,902 | 1/1981 | Martinez | 604/22 |
| 4,314,560 | 2/1982 | Helfgott et al. | 128/305 |
| 4,530,359 | 7/1985 | Helfgott et al. | 128/329 R |

Primary Examiner—Richard J. Apley
Assistant Examiner—H. Macey
Attorney, Agent, or Firm—Erwin S. Teltscher

[57] ABSTRACT

Device for perforating the lens capsule front wall in the eye of living beings for removing a part of the capsule wall and producing an opening through which the lens capsule contents can be removed. A tube is arranged on a hand piece, in which a wire provided with a point on its free end is held, said wire being connected to a drive motor putting the wire in axially reciprocating motion.

10 Claims, 4 Drawing Figures

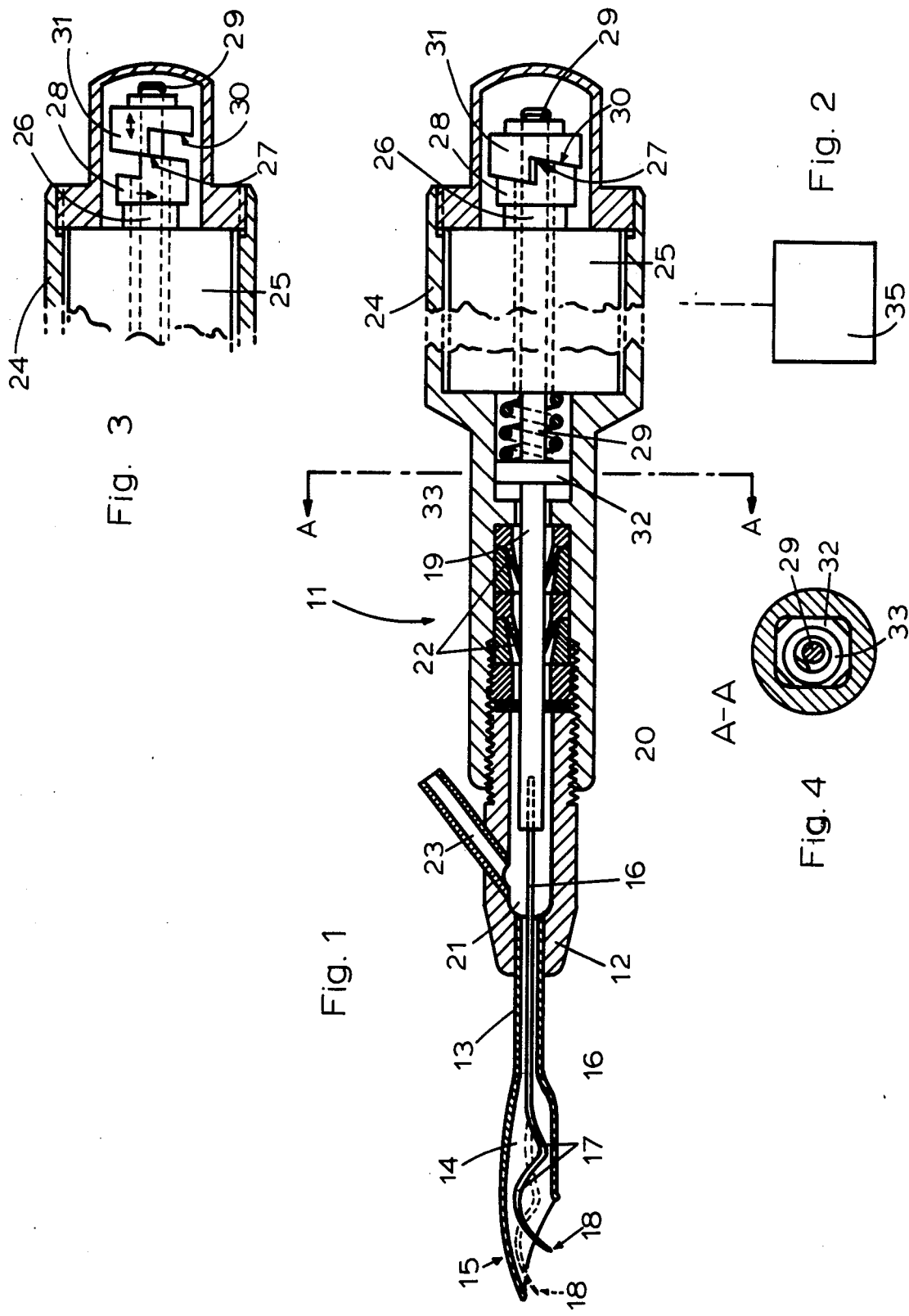

DEVICE FOR PERFORATING THE LENS CAPSULE FRONT WALL IN THE EYE OF LIVING BEINGS

BACKGROUND OF THE INVENTION

The invention refers to a device for perforating the lens capsule front wall in the eye of living beings for removing a part of the capsule wall and producing an opening therein, through which the lens capsule contents can be removed.

Up to now it has been common practice to open the lens capsule sack by means of most varied instruments, wherein, however, as a rule the edge of the opening cut into the front wall of the lens body sack has a more or less irregularly jagged or frayed shape. However, this is disadvantageous, especially with regard to surgical measures to insert an implantation lens in the patient.

For a long time the wish has existed to have a device which is in the position to cut out a circular disc of a certain size from the front wall of the lens capsule sack, in order to obtain a circular opening with a smooth, unjagged edge along the incision line. Devices which enable this have not become known up to now, for which reason the invention is based on the task of creating such a device which is able to carry out the task given above.

For the solution of this task it was proposed to design the device in question in such a way that an annular guideway is located on or in a cutting head insertable into the opened eye, along which guideway a cutting knife projecting beyond the guideway in an axial direction and making a circular incision during its movement is guided.

To be sure, the aforementioned device carries out its task in a quite satisfactory manner; however, conditioned by its mechanical construction, it is extraordinarily delicate and thus susceptible to breakdowns. Therefore, it is unsuitable as a device to be used in the operations in question.

SUMMARY OF THE INVENTION

The invention is based on the task of creating a device suitable for the purpose mentioned, constructively simple and dependably working, always ready for use, which makes it possible to open the lens capsule quickly and dependably in the desired, optimal manner, so that a hole in the front wall is obtained, which is located at the place at which it is desired, and which is defined with regard to its size and shape. Herein, in addition, the hydrostatic pressure in the front chamber of the eye should be maintained during the use of this device, in order to enable work in an optimal operating field.

The for solution of this task the proposal according to the invention is to design the device in question in the manner as described and shown in particular in patent claim 1 and furthermore in the the independent claims, dependent claims, as well as with reference to a preferred embodiment.

BRIEF DESCRIPTION OF THE DRAWING

FIG. 1 of the drawing drawing shows a longitudinal section through the device designed according to the invention;

FIG. 2 shows schematically alternate pneumatic drive means;

FIG. 3 corresponds to a rear portion of FIG. 1, but shows the drive ring in a frontmost position; and FIG. 4 is a cross-section along line A—A of FIG. 1.

The inventive device or surgical instrument consists of a hand piece 11, on the front part 12 of which a tube 13 is coaxially attached. The front end 14 of the tube 13 is pressed somewhat flat and is provided with a curve 15. In the tube 13 an axially oscillating, movable wire 16 is mounted with relatively large play, the wire being wavily bent and provided with a point 18 at its front end 17.

The wire 16 is connected with its rear end to a shaft or piston 19, which projects with its front end 20 into the chamber 21 in the hand piece 11, which chamber is sealed towards the rear against the piston 19 by means of sealing collars 22. A connection piece 23 disposed on the hand piece opens into the chamber 21, onto which connection piece a hose can be fitted to convey liquid under predetermined pressure into the chamber 21, which liquid then exits during use of the device through the tube 13 guiding the wire and at its front end, to maintain a certain hydrostatic pressure in the opened front chamber of the eye to be operated on, which substantially facilitates and/or promotes the operation in the opened eye.

The lens capsule front wall is perforated with the point 18 at the front end of the wire 16 along a line, usually a circle, determined by the operator, wherein the punctures lie in close juxtaposition to each other. This is achieved by moving the wire 16 back and forth at a certain frequency, for instance of approximately 30–80 Hz. Both an electromagnet and an electric motor can be used as drive aggregate, provided that the motion characteristics are such that the point 18 of the oscillating wire 16 is able to surely penetrate the capsule wall in its advance. The axial movements of the wire 16 are not supposed to follow a sinus function, as its point 18 has the lowest speed and acceleration values at the points of motion reversal. Since the lens capsule consists of an extrordinarily tough and resistant tissue, in order to achieve good working results, the wire point 18 must be shot forward very spontaneously, in order to thus abruptly penetrate the lens capsule wall.

In order to achieve this, a drive aggregate is preferably used which consists of a drive motor with rotating rotor and a relatively simple mechanism which draws back the piston 21 and thereby the wire 16, and in doing so simultaneously tenses a spring acting thereupon, which upon being suddenly released shoots the wire 16 forward in the desired manner.

At the rear end of the hand piece 11 there is an electric motor 25 in a housing 24, the hollow shaft 26 of which motor causes a drive ring 28 provided with first cam means, such as a curve path 27 to rotate along a direction shown by an arrow 28'. Abutting this is a drive disc 31 axially connected with the drive shaft 29 and likewise provided with a corresponding curve path 30, which drive disc 31 cooperates with the drive ring 28, and is axially moved back during one revolution of the drive ring 28, wherein it draws back the drive shaft 29. It thus executes a reciprocal movement, as shown by the double arrow. A spring plate 32 by which the spring 33 is tensed is located on the drive shaft and axially connected thereto. With the corresponding movement of the drive ring 28 relative to the drive disc 31, drive disc 31 moves away rearwardly the drive ring 28, so that the spring 33 can then drive the drive shaft 29 abruptly forward, taking along the spring plate 32, The pointed wire 16 is therefore caused to move reciprocally between the points 18 and 18'. Instead of the drive ring being actuated by the electric motor 25, it can alternately be actuated by pneumatic or hydraulic means, such as drive means 35, shown only schemtically in FIG. 2.

What is claimed is:

1. Surgical instrument for perforating the front wall of the lens capsule in the eye of living beings for removing a piece of the capsule wall and producing an opening through which the lens capsule contents can be removed, comprising in combination an elongated hollow handpiece, an elongated tube disposed near a front end of said handpiece, having an opening near the front end of said handpiece, and at least partially fitting into said handpiece, an elongated wire located in said tube, being movable between axially frontal and retracted positions, and having one pointed end extended in a frontal direction through the opening of said tube in said frontal position, a drive motor connected to said wire, and means associated with said drive motor for reciprocally moving said wire between said frontal and retracted positions so that said wire is moved relatively slowly from said frontal position to said retracted position, but is aburptly moved forwardly from said retracted position to said frontal position.

2. The surgical instrument as claimed in claim 1, wherein said wire has an outside diameter and said tube has an inside diameter exceeding the outside diameter of said wire by a factor of at least two.

3. The surgical instrument as claimed in claim 1, wherein said wire has at least one curved portion at least near the pointed end thereof, and said tube has an inner curved portion, so that the curved portion of said wire is slidably disposed within the inner curved portion of said tube.

4. The surgical instrument as claimed in claim 3, wherein said tube has an oval cross-section near a front end thereof, and wherein said wire has another curved portion adjoining said one curved portion, said wire portions having an S-shaped configuration.

5. The surgical instrument as claimed in claim 1, wherein said tube defines a chamber, a further comprising a connection piece connected to said tube, extending outwardly beyond said tube, and communicating with said chamber, whereby a hose can be fitted onto said connection piece, and liquid with a predetermined pressure can be passed through said connection piece to maintain said pressure in the opened front chamber of the eye to be operated upon.

6. The surgical instrument as claimed in claim 5, wherein said means associated with the drive motor for reciprocally moving said wire includes a piston movable through at least a portion of said tube outside of said chamber, and further comprising sealing means for sealing said outside portion from said chamber, while permitting axial movement of said piston inside said tube.

7. The surgical instrument as claimed in claim 6, wherein said sealing means include a collar provided with a sealing lip abutting said piston.

8. The surgical instrument as claimed in claim 1, wherein said drive motor includes a hollow shaft, and wherein said means associated with the drive motor for reciprocally moving said wire include a piston axially movable through said handpiece, a plate connected to one end of said piston remote from said tube opening, a drive shaft connected to said plate and slidable through the hollow shaft of said drive motor, said drive shaft extending in a direction away from said tube opening through the beyond said hollow shaft, a drive ring rigidly connected with said drive motor, and slidably disposed on said drive shaft near an end thereof and remote from said plate, a spring interposed between said plate and a face of said drive motor facing said tube opening, a drive disc mounted on said drive shaft near said end thereof remote from said tube opening, and being axially movable with said drive shaft, and first cam means mounted on said drive disc and second cam means mounted on said drive ring cooperating with one another so that as said drive ring moves towards an axially extreme rearward rotational position during one rotation thereof, and said cam means only abut one another, but are out of engagement with one another, said drive disc is forced relatively slowly rearwardly in a direction away from said tube opening, causing said wire to assume said retracted position, but as said drive ring reaches an axially extreme frontward rotational position so that cam means can be brought into engagement with one another, said drive disc is abruptly pulled in a direction towards said tube opening by the force of said spring, so that said wire is abruptly pushed forwardly into said frontal position.

9. The surgical instrument as claimed in claim 1, wherein said drive motor includes pneumatic drive means.

10. The surgical instrument as claimed in claim 1, wherein said drive motor includes hydraulic drive means.

* * * * *

UNITED STATES PATENT OFFICE
CERTIFICATE OF CORRECTION

Patent No. 4,706,669　　　　　　　　Dated Nov. 17, 1987

Inventor(s) Hans Joachim Schlegel

It is certified that error appears in the above-identified patent and that said Letters Patent are hereby corrected as shown below:

Inventor's Address; item [76] on first page of Patent should read:

--Max Planck- Str. 5, Hamburg, Fed. Rep. of Germany--

Signed and Sealed this

Thirty-first Day of May, 1988

*Attest:*

DONALD J. QUIGG

*Attesting Officer*　　　　*Commissioner of Patents and Trademarks*

UNITED STATES PATENT OFFICE
CERTIFICATE OF CORRECTION

Patent No. 4,706,669                    Dated November 17, 1987

Inventor(s) Hans Joachim Schlegel

It is certified that error appears in the above-identified patent and that said Letters Patent are hereby corrected as shown below:

Title page:

Inventor's Address; item [76] on first page of Patent should read:

--Max Planck- Str. 5, 6650 Homburg/Saar, Fed. Rep. of Germany--

This certificate supersedes certificate of correction issued May 31, 1988.

Signed and Sealed this

Thirteenth Day of December, 1988

Attest:

DONALD J. QUIGG

Attesting Officer          Commissioner of Patents and Trademarks